United States Patent [19]
Sinnett

[11] Patent Number: 6,075,449
[45] Date of Patent: Jun. 13, 2000

[54] PERFORMANCE INDICATOR FOR AN ELECTRICAL STATIC ELIMINATOR DEVICE

[75] Inventor: Chandler G. Sinnett, Falmouth, Me.

[73] Assignee: Chapman Corporation, Portland, Me.

[21] Appl. No.: 09/084,756

[22] Filed: May 26, 1998

[51] Int. Cl.⁷ .................................................. G08B 21/00
[52] U.S. Cl. ......................... 340/657; 340/660; 340/664; 340/635; 324/519; 324/522; 324/750; 361/212; 361/222; 361/230
[58] Field of Search .................................. 340/657, 660, 340/664, 635; 324/519, 522, 750; 361/220, 212, 222, 230

[56] References Cited

U.S. PATENT DOCUMENTS

| | | | |
|---|---|---|---|
| 4,745,519 | 5/1988 | Breidegam | 361/220 |
| 5,017,876 | 5/1991 | Wright et al. | 324/464 |
| 5,570,266 | 10/1996 | Testone | 361/229 |

*Primary Examiner*—Julie Lieu
*Attorney, Agent, or Firm*—Iandiorio & Teska

[57] ABSTRACT

An electrical static eliminator device performance indicator including a sensor for sensing the ion flow from an emitter point of the static eliminator device and also for sensing the presence of a voltage at an emitter point to accurately detect the fouling of a point or shorted point condition; a display, responsive to the means for sensing, for displaying an indication of a fouled emitter point or a shorted emitter point; and an electrical circuit interconnecting the sensor and the display.

14 Claims, 8 Drawing Sheets

PERFORMANCE INDICATOR FOR AN ELECTRICAL STATIC ELIMINATOR DEVICE

FIELD OF INVENTION

This invention relates to an electrical static eliminator device performance indicator which is hand held, mobile, compact, passively powered, simple in design, and yet which accurately detects whether any emitter point of a static eliminator device is fouled or shorted and which, in addition, can be used either on the front or the back side of static eliminator devices such as ionizing bars to indicate the presence or absence of ion flow from ionizing emitter points.

BACKGROUND OF INVENTION

Electrical static eliminator devices such as ionizing bars, ionizing blowers, and single point static eliminators function to eliminate static electricity by emitting ions into the area proximate a surface or device carrying undesirable static charges. Ionizing bars, for example, are typically employed in printing machinery and used to prevent particles from contaminating the paper during the printing process and to prevent handling or processing problems. Ionizing blowers, on the other hand, are typically used at electrostatic discharge (ESD) safe work stations to prevent electrostatic discharge damage to sensitive electrical components.

The prior art methods of checking the performance of such static eliminator devices are severely limited. In one example, an indicator lamp is provided and powered by the same power supply which provides power to the static eliminator device. If power is supplied to the static eliminator device, the lamp is illuminated. Thus, this lamp only indicates whether power is being supplied from the secondary transformer of the power supply. Therefore, it provides no indication of whether each emitter point of the static eliminator device is actually ionizing and thus provides a false positive indication when an individual emitter point is fouled with particulate matter, disconnected from the transformer, and/or grounded. In a given manufacturing facility, it is not uncommon for one or more emitter points to become fouled over time or shorted thus severely reducing the performance of the static eliminator device.

In another prior art device, a capacitive plate is permanently incorporated on the end of the body of an ionizing bar and a lamp is connected to the capacitive plate. This device lets the user know whether or not voltage is being applied all the way along the bar, but, again, provides a false positive reading if one or more individual emitter points are fouled or shorted and thus not ionizing.

Such prior art devices fail to sense both the ion flow from each point of the static eliminator device and the presence of a proper voltage at such an ionizing point to thus accurately detect both the fouled point condition and a shorted point condition.

Also available are other prior art devices which include a family of laboratory and hand-held devices that typically incorporate an electrostatic voltage metering device with a plate which can be charged. The ability of the static eliminating device to discharge the plate is monitored. The typical size of the plate utilized is too large to discern problems with individual ionizing points, and the typical testing method must allow for charging and decay times that do not permit prompt analysis of the performance level of individual ionizing points. Also, these prior art devices typically include rather complex circuitry, require a power source, and are thus expensive to manufacture. Examples of prior art indicators include U.S. Pat. Nos. 5,570,266 and 5,017,876 incorporated herein by this reference.

SUMMARY OF INVENTION

It is therefore an object of this invention to provide an electrical static eliminator device performance indicator which is capable of sensing, depending on how it is utilized, the ion flow from any emitter point of the static eliminator device and also the presence of a voltage sufficient to create ionization at each emitter point to accurately detect both the fouling of an emitter point and a shorted emitter point condition to eliminate the inaccurate false positive readings of prior art indicators.

It is a further object of this invention to provide such a performance indicator which is simple in design.

It is a further object of this invention to provide such a performance indicator which does not require complex electrical circuitry.

It is a further object of this invention to provide such a performance indicator which is hand held, mobile, and compact.

It is a further object of this invention to provide such a performance indicator which is powered by the static eliminator device itself and thus requires no separate power supply.

This invention results from the realization that a performance indicator which is hand held, mobile, compact, passively powered, simple in design, and which accurately detects whether the points of a static eliminator device are fouled or shorted can be effected by a small hand held housing which incorporates a liquid crystal display, a simple voltage divider circuit, and a conductive sensor which, in combination with the voltage divider circuit and the liquid crystal display, senses and provides an indication of both the ion flow from each emitter point of a static eliminator device and the presence of the proper voltage at each emitter point to accurately detect both fouled emitter point and shorted emitter point conditions.

This invention features an electrical static eliminator device performance indicator comprising means for sensing both the ion flow from one or more emitter points of the static eliminator device and the presence of a voltage at one or more emitter points to accurately detect both the fouling of a point and a shorted point; a display, responsive to the means for sensing, for displaying an indication of a fouled point or a shorted point; and an electrical circuit interconnecting the means for sensing and the display.

The display is typically a liquid crystal display. The electrical circuit may include a first resistor connected between the display and ground for removing residual charges from the display. The electrical circuit may also include a voltage divider which has a second resistor connected between the sensor and the display. The means for sensing may be a simple conductive plate. In the preferred embodiment, a housing integrates the conductive plate, the display, and the electrical circuit in a mobile, compact fashion for sensing the performance of the static eliminator device along its length. The housing renders the indicator capable of being held in the hand of the user.

The housing typically has a window on one surface thereof for viewing the display and a set of depending legs configured to engage a shield portion of the static eliminator device and to position the means for sensing a predetermined distance from the emitter points of the static eliminator device.

A slidable electrical static eliminator device performance indicator according to this invention has both a housing and means for sliding the housing along the length of the static eliminator device. The housing includes means for sensing both the ion flow from an emitter point of the static eliminator device and the presence of voltage at an emitter point to accurately detect both the fouling of a point and a shorted point, and a display, responsive to the means for sensing, for displaying an indication of a fouled point or a shorted point. The means for sliding the housing along the static eliminator device positions the means for sensing a predetermined distance from the body of the static eliminator device to provide an indication of whether each emitter point of the static eliminator device is ionizing. The means for sliding typically includes at least one clip attached on one end to the housing having another end configured to slidably engage the static eliminator device. An optional extender may be attached to the sensor and thus varying its spatial relationship with respect to an emitter point when, for example, the indicator is used on the back of an ionizing bar.

DISCLOSURE OF PREFERRED EMBODIMENT

Other objects, features and advantages will occur to those skilled in the art from the following description of a preferred embodiment and the accompanying drawings, in which.

Figure 1:
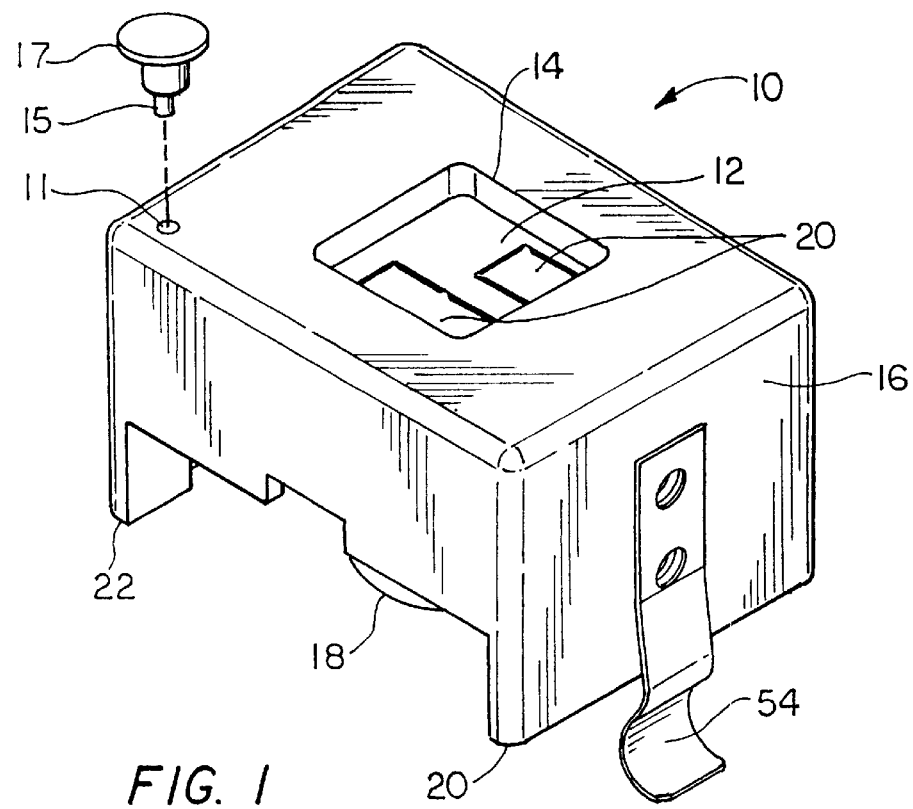
FIG. 1 is a three dimensional diagrammatic view of the performance indicator for an electrical static eliminator device in accordance with the subject invention.

Hand held, mobile, compact, passively powered electrical static eliminator device performance indicator 10, FIG. 1 of this invention includes a display such as liquid crystal display (LCD) 12 viewable through window 14 in housing 16 and connected to means for sensing 18. Such an LCD in the preferred embodiment is a low current display as opposed to a lamp or bulb thus facilitating the passively powered feature of the subject invention. Means for sensing 18 may be a conductive (e.g. aluminum) sensor plate 0.25" wide by 0.75" long as shown in more detail in FIG. 2 which uniquely senses both the ion flow from each emitter point of a static eliminator device and also the presence of the proper voltage at each emitter point to accurately detect both the fouling of an emitter point and a shorted emitter point.

Figure 2:
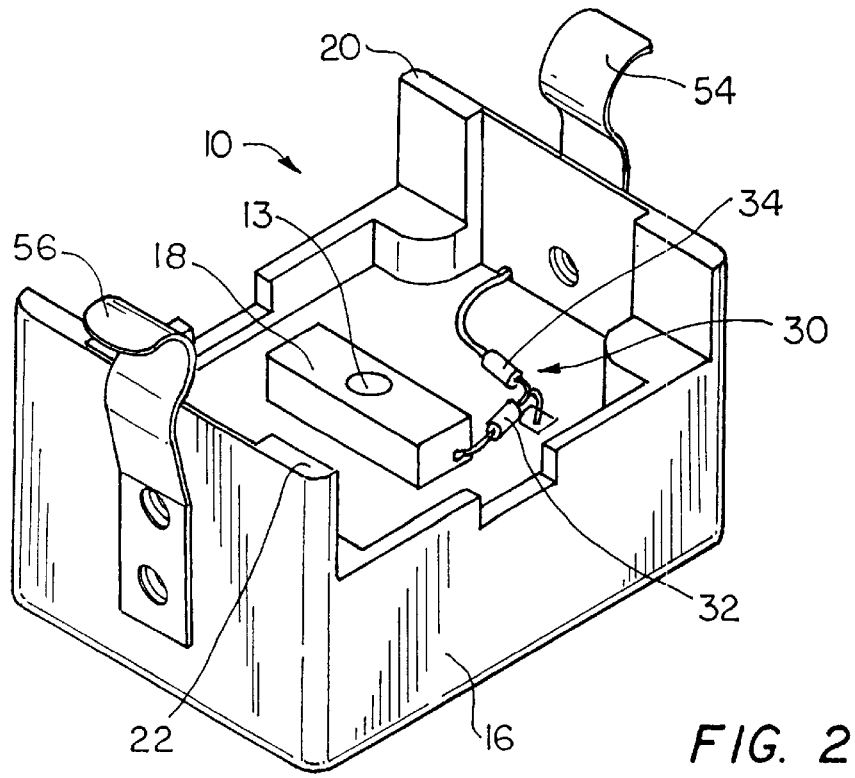
FIG. 2 is a three dimensional diagrammatic view of the interior portion of the performance indicator shown in FIG. 1.

LCD display 12, FIG. 1 is capable of providing an unmistakable "on" indicia 20 in response to sensor 18 but in alternative embodiments may simply be one or more lamps or even a bar graph. Housing 16 is typically also made of aluminum and includes a set of depending legs 20 and 22 configured to engage the shield portion of a typical ionizing bar to position sensor 18 at a predetermined distance (e.g., 0.050–1.000 inches) from the emitter points of the ionizing bar. Clips 54 and 56 secure housing 16 to the shield portion of a typical static eliminating bar. Optional sensor extender 17 includes post 15 for storing extender 17 on body 16 of indicator 10 via orifice 11 which receives post 15 of extender 17. Sensor 18, FIG. 2 includes a similar orifice 13 for receiving post 15, FIG. 1 of extender 17. Also forming the part of indicator 10, FIG. 2 is electrical circuit 30 interconnecting sensor 18, FIGS. 1 and 2, and display 10, FIG. 1. Electrical circuit 30 will vary somewhat depending on the selection of display 12 but in one embodiment includes resistors 32 and 34 forming a voltage divider circuit discussed with reference to FIG. 3. Electrical circuit 30 powers display 12 to provide an "ON" indicia when the emitter points of the static eliminator device are properly ionizing and when the proper voltage is present at each emitter point.

Housing 16, FIGS. 1 and 2 renders indicator 10 hand held, compact, and slidable along the length of an ionizing bar in that it integrates sensor 18, electrical circuit 30, and display 12. Electrical circuit 30, shown in more detail in FIG. 3, includes resistors 32 and 34 forming a voltage divider circuit. Resistor 34 (e.g. 1 MΩ), connected between LCD 12 and ground, operates to remove residual charges from LCD 12 and to speed up the response rate. It is possible that for some designs and for particular LCDs, the parasitic internal resistance of the LCD may be adequate for the timing needed. In these cases, resistor 34 may not be required. Depending on the size of sensor 18, and for large sensor plate areas and/or strong signals, resistor 32 (e.g. 10 MΩ), connected between sensor 18 and LCD 12, may also be required as part of a voltage divider to present the proper voltage to LCD 12. Resistor 32 is also required when voltage division is needed. Also, resistor 32 helps to assure longer LCD life. When either of these requirements are not needed, resistor 32 may be effectively zero or eliminated. The terminal connections of LCD 12 may vary depending on the model used. When the LCD model chosen has elements available that are not shown as part of the indicia 20, FIG. 1, they are grounded to prevent confusing displays. One relatively common LCD is designed to display 2 digits using 7 segments each, with two decimal points available. The pin-out for one such model can be connected to display "On" by connecting pins 3, 4, 5, 7, 9, 14, 15, and 16 to the voltage divider 30, and connecting the remaining pins (of 18 pins) to ground.

Figure 4:
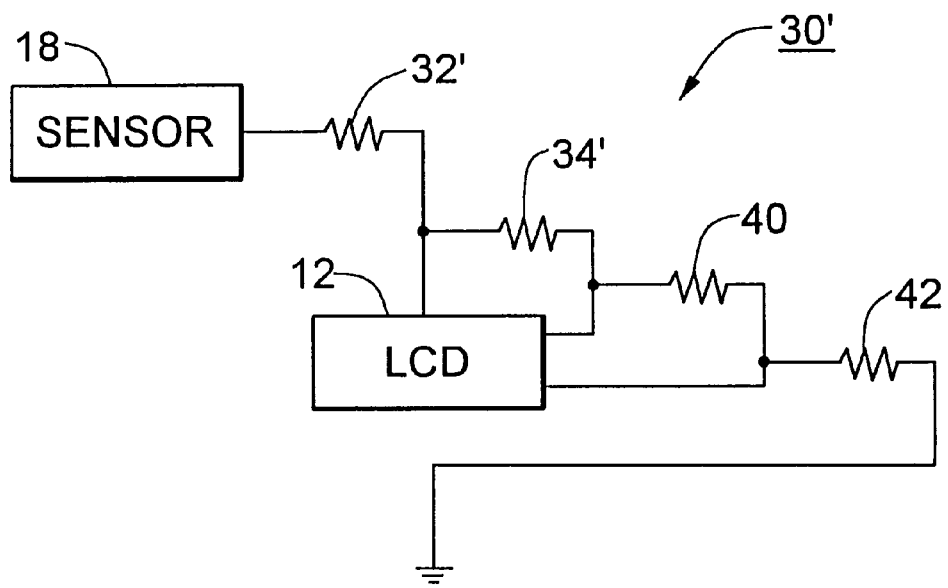
FIG. 4 is a schematic diagram of an alternative embodiment of the electrical circuit portion of the performance indicator shown in FIGS. 1 and 2.

Alternative resistor divider network 30', FIG. 4, includes resistors 34', 40, and 42 (other similar resistors may be added) and are chosen to provide some gradation in the response dependent on the gradation in the signal. When such a system is used, a bar graph output display may be preferred or the available LCD elements may be selected such as to display a variety of different indicia.

The signal referred to so far detected by sensor 18, FIGS. 1 through 4 is derived in two ways. First, the signal can be based on an AC capacitive coupling action from the high voltage present in the body of a static eliminating bar or a cable created on the close proximity of indicator 10, FIG. 1 to that voltage. Alternatively, and in addition, the sensor signal can be based on an AC flow of ions from an emitter point which occurs as sensor 18 is placed close to such a point. At the proper range and size of sensor 18, meaningful information can be obtained about each emitter point. Alternatively, the size and shape of sensor 18, FIG. 2 may be configured to provide this information for a plurality of emitter points to be arranged. Resistor divider network 30, FIG. 3, or 30', FIG. 4, protects the LCD from damage and allows easy selection of a preferred relationship between the sensor size and the distance to the signal source with the proper voltage to the LCD. The LCD is wired to use this voltage to activate certain elements. In the economical version, a commercially available LCD with two seven segment displays can be wired to display an "On" indicia when the proper voltage is present.

Housing 16, FIG. 1 provides protection for this voltage divider circuit and also provides a ground return. The ground return is either a direct coupling of the housing to grounded surfaces by actual contact, AC capacitive coupling of the indicator housing to a grounded surface due to a close proximity of those surfaces, or a combination of both types of grounding mechanisms.

Figure 5:
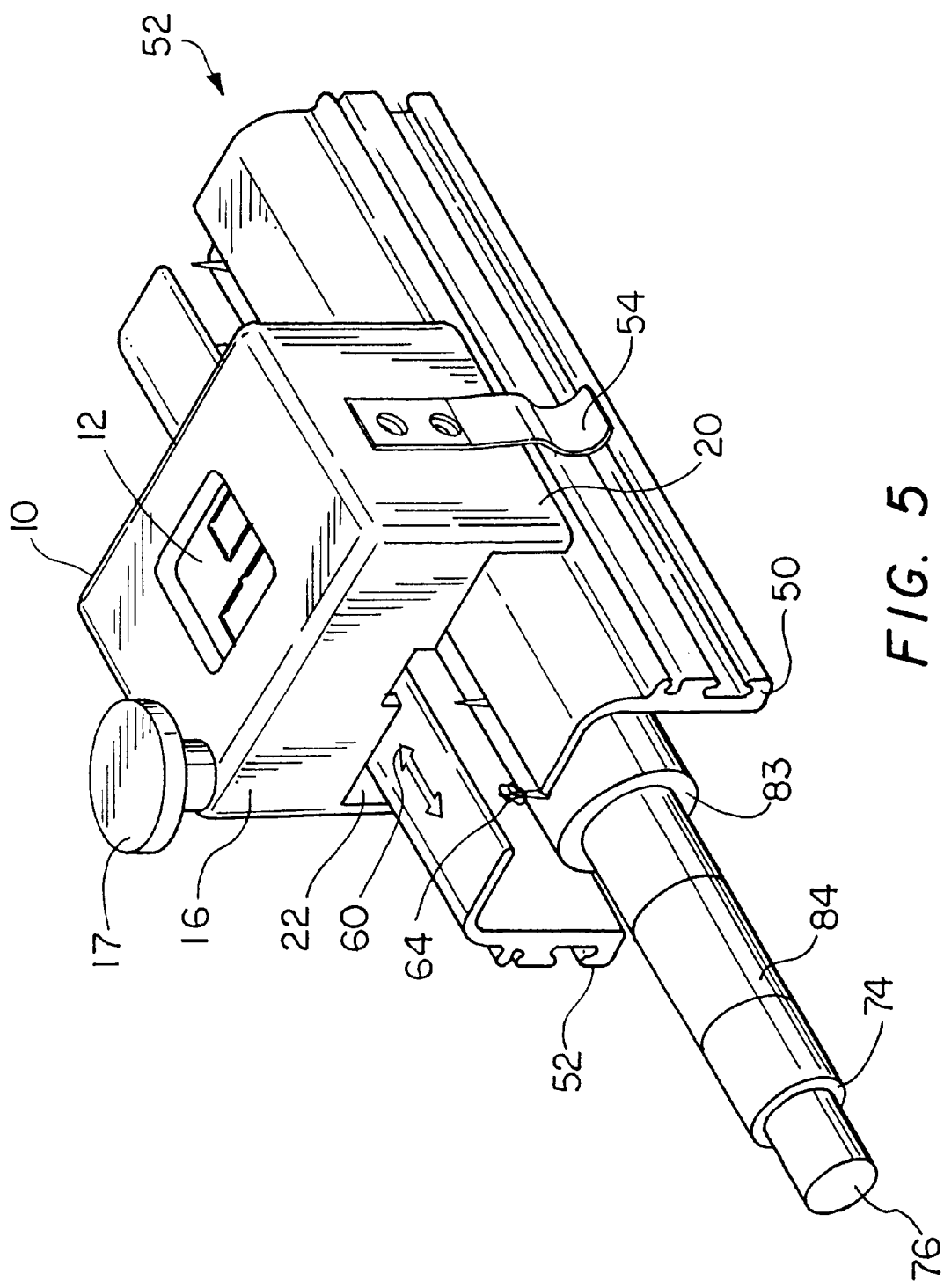
FIG. 5 is a three dimensional diagrammatic view of the performance indicator shown in FIGS. 1 and 2 in place and slidably engaged with the front of an ionizing bar in accordance with the subject invention and also showing the storage position of the optional extender device in accordance with the subject invention.

In operation on the front of ionizing bar 52, FIG. 5, sensor 10 is slidably engaged with shield portion 50 via clips 54 and 56 (see FIG. 2) which provide a means for sliding the legs 20 and 22 of housing 16 along the length of bar 52 in the direction shown by arrow 60. In this way, if emitting point 62 is fouled with particulate matter 64 and not ionizing, display 12 will not be energized and thus will not display a positive "On" working indication when sensor 10 is positioned over emitter point 62. The same result occurs if emitting point 62 (or any other point) is shorted to ground. Thus, indicator 10 uniquely checks whether each emitting point and every emitting point is ionizing and whether there is a sufficient voltage at each point to cause ionization. Ionizing bar 52 is of typical construction and includes central conductor 76, high voltage insulator 74, conductive band 84, and insulating body 83 which supports emitter point 62.

Figure 6:
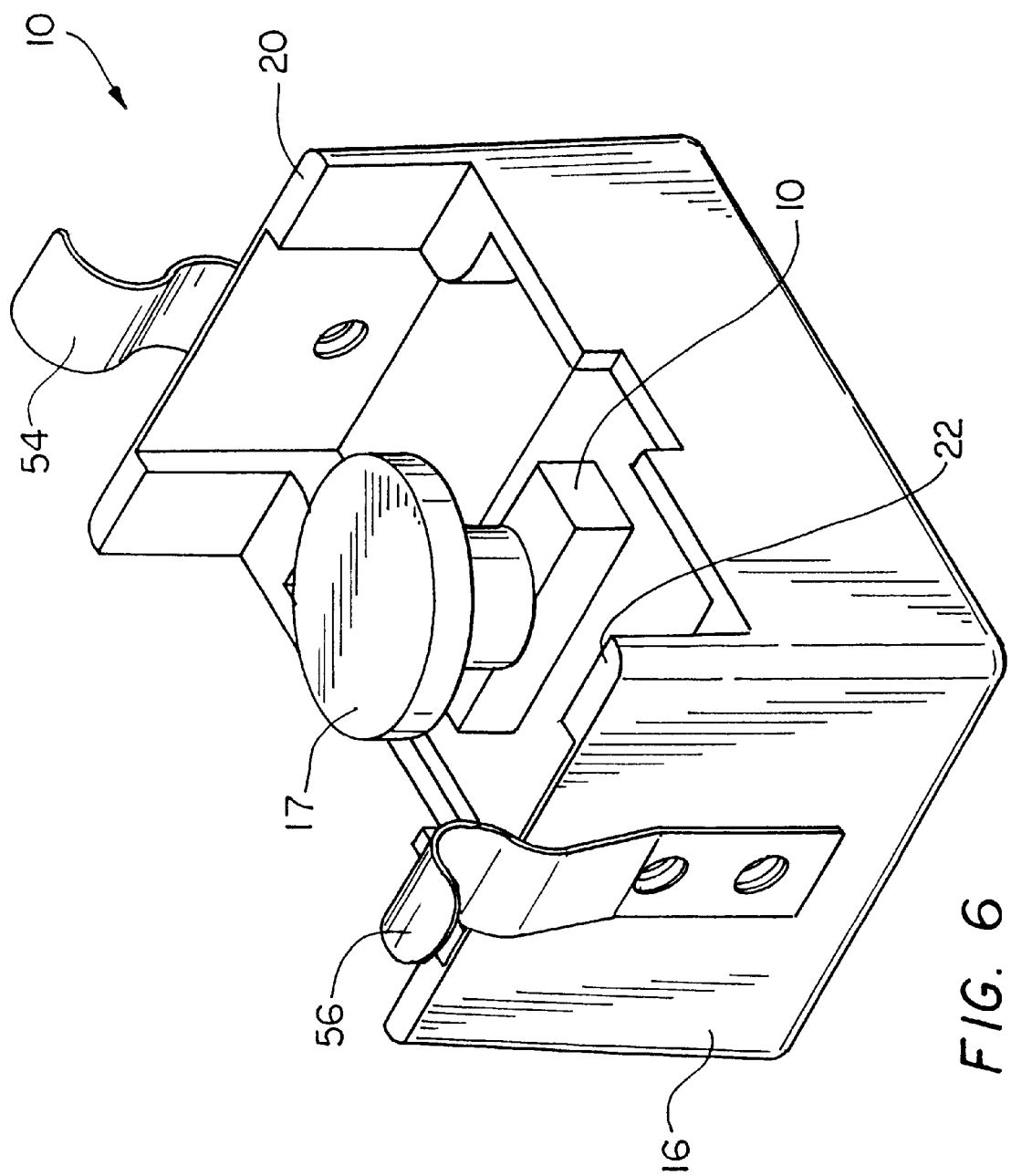
FIG. 6 is a three dimensional diagrammatic view of the indicator of this invention with the extender device in place on the sensor.
Figure 7:
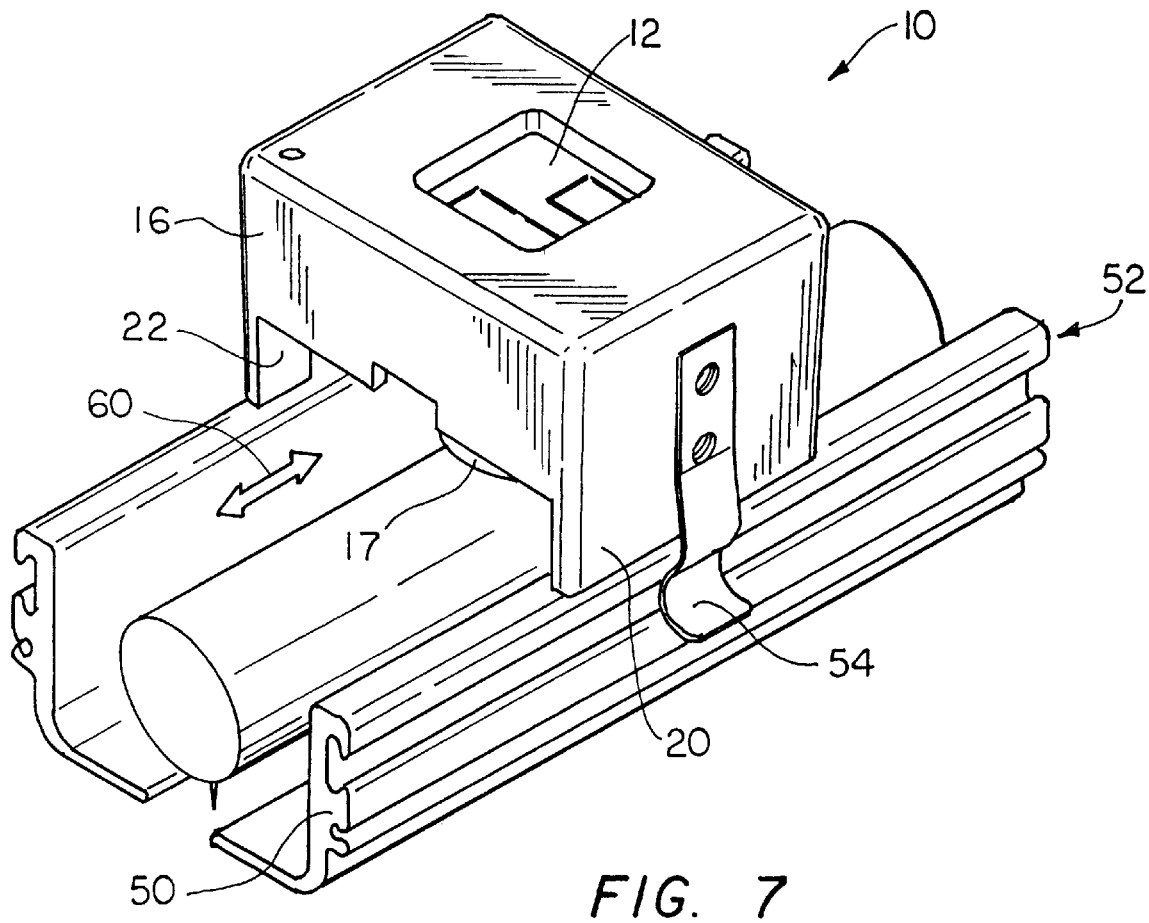
FIG. 7 is a view similar to FIG. 5 of the performance indicator shown in FIGS. 1 and 2 slidably engaged with and placed on the back on an ionizing bar in accordance with the subject invention.
Figure 8:
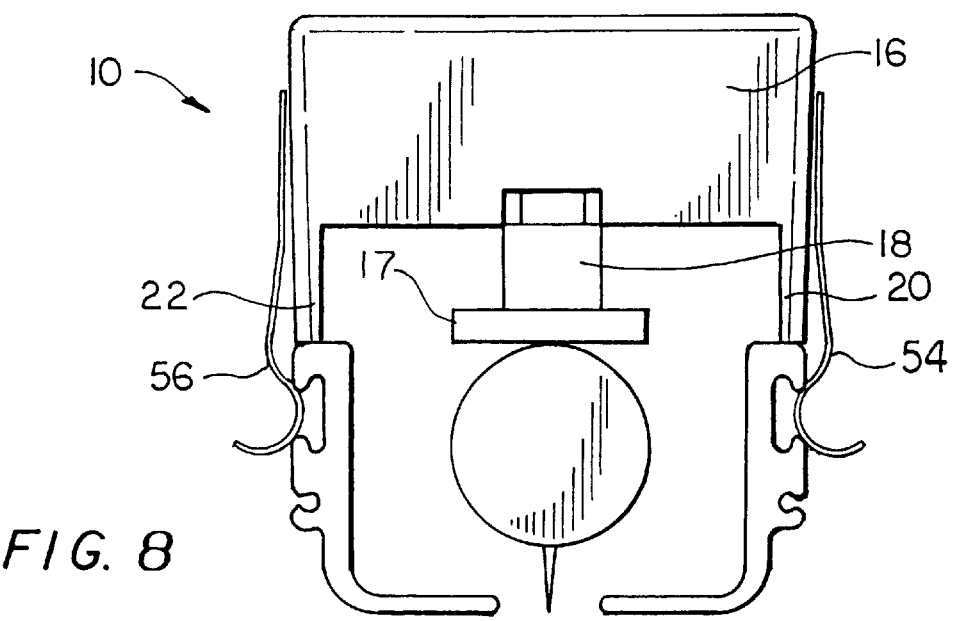
FIG. 8 is an end view of the indicator of this invention showing the operation of the optional extender device in accordance with the subject invention.

In operation on the back of an ionizing bar, useful in situations when the front of the ionizing bar is not accessible because of its location relative to a web roller or the like, sensor extender 17, FIGS. 6, 7 and 8 is used to effectively extend the length of sensor 10. LCD 12, FIG. 7 will be energized and will provide an "On" indicia when the proper AC high voltage is being received at each point along the ionizing bar and also when the points along the bar opposite where the indicator is clipped are not shorted ground. Clips 54 and 56 are also used to maintain leg 20 about shield portion 50 when indicator 10 is engaged with the back of ionizing bar 52.

In another embodiment, clips 54 and 56 may only be accessories and indicator 10 may be used as a hand held unit and moved along the front of the ionizing bar as shown in FIG. 5 to indicate whether the proper high voltage is getting to the bar, that each emitting point band, as the unit is slid along the bar, is not shorted to ground, and that each emitting point, as the unit is slid along, is ionizing. As the indicator is slid along the length of the bar on the back side of the bar as shown in FIG. 7, LCD 12 will show "On" to indicate that the proper high voltage is getting to the bar and that each point band as the unit is slid along, is not shorted to ground.

Modular, hand held, passively powered, and compact indicator 10 provides the user with many different options. Clipped to the bar, and held stationary, information is provided visibly to the user easily and continuously. The operator can then move the indicator via the sliding clips to check the whole bar from the back and the front sides. When the clips are not used at all, the operator can carry indicator 10 in his hand and check a number of bars on the manufacturing floor either from the front and/or the back as space allows. Indicator 10 may also be used to detect an AC high voltage through the insulation of a wire or unshielded cable. When sensor 18 is placed in contact with such a wire, display 12 will indicate "On". This configuration allows continuous monitoring of the output from AC power supplies which may be especially useful in cases where the process equipment does not have a space for mounting the unit in the clips or when the operator can not view such a location. Still another use of indicator 10 is to detect AC signals which may result from a voltage divider circuit external to the sensor. Thus, the high voltage divider may be connected directly to the output of a power supply and indicator 10 may be utilized to provide an indication of "On" when power is present.

Thus, indicator 10 of this invention is uniquely capable of sensing both the ion flow from any emitter point of a static eliminator device and also the presence of a voltage at a point to accurately detect both the fouling of a point and a shorted point to eliminate the false positive readings of prior art indicators. Indicator 10 is simple in design and eliminates the need for complex electrical circuitry. Indicator 10 is also hand held, mobile, compact, simple in design, and passively powered thus eliminating the need for batteries.

Figure 3:
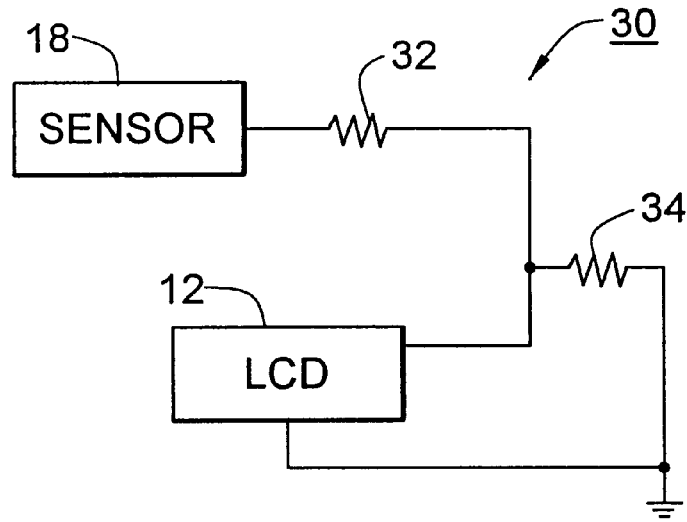
FIG. 3 is a schematic diagram of one embodiment of the electrical circuit portion of the static indicator device shown in FIGS. 1 and 2.

Indicator 10 accurately detects whether the points of a static eliminator device are fouled or shorted by the combination of small hand held housing 16, FIG. 1 which incorporates liquid crystal display 12, simple voltage divider circuit 30, FIGS. 2–4, and conductive sensor 18 which in combination with the voltage divider circuit and the liquid crystal display senses both the ion flow from any emitter point of the static eliminator device and the presence of a voltage at any emitter point to accurately detect both the fouling of a point and a shorted point.

Figure 9:
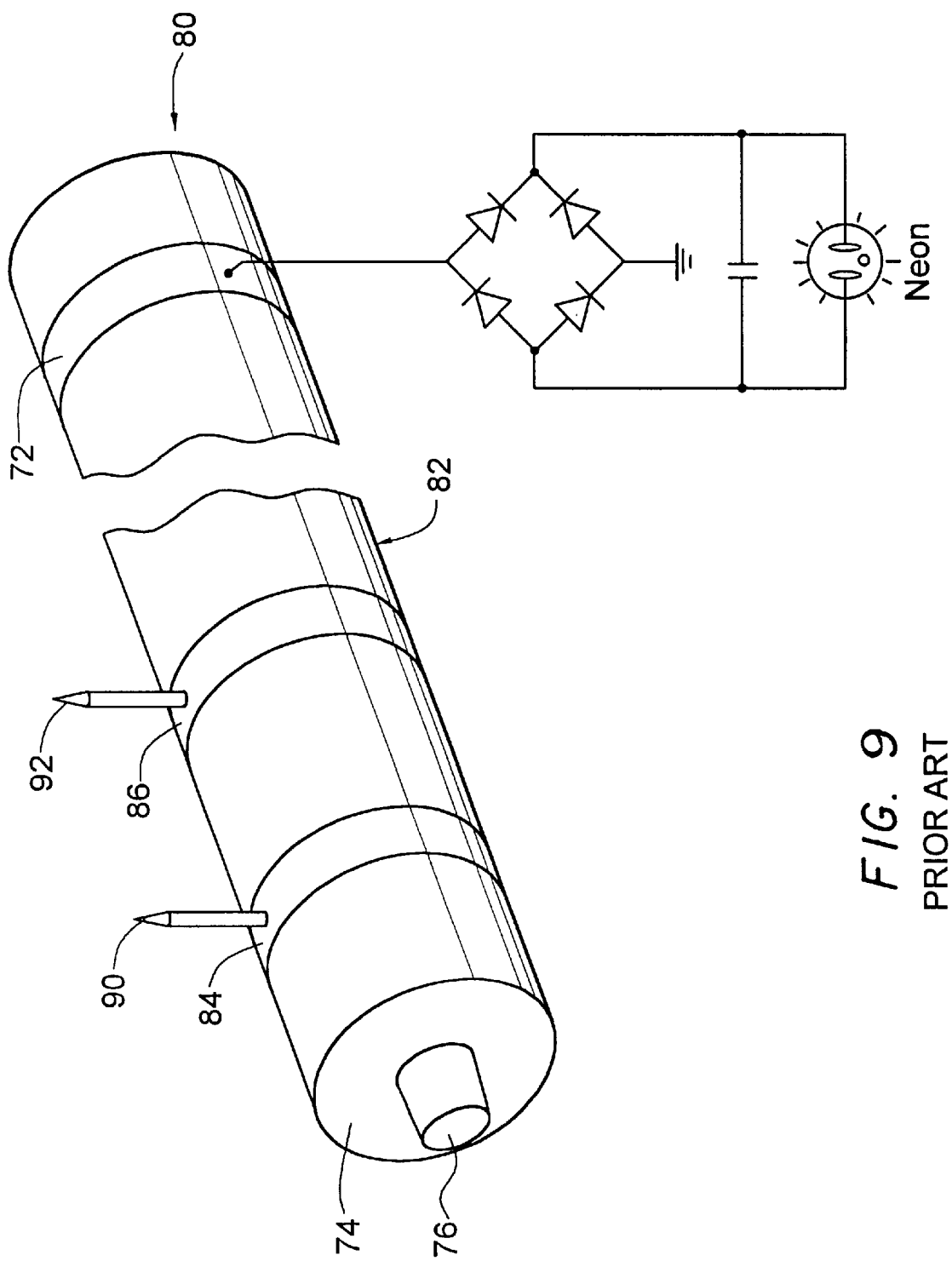
FIG. 9 is a schematic view of an ionizing bar body incorporating a permanently attached prior art performance indicator system.

In contrast, prior art indicator 80, FIG. 9 includes fixed conductive plate 72 disposed about insulator 74 surrounding conductor 76 of ionizing bar body 82. Lamp 76 connected via circuit 78 to plate 72, at best, only provides an indication of whether a voltage is present at end 80 of ionizing bar body 82. If emitter point 90 connected to plate 84 is fouled and/or point 92 connected to plate 86 is grounded, this non-ionizing condition will not be detected by prior art indicator 80. Thus, unlike indicator 10, FIG. 1 of this invention, prior art indicator 89 is not slidable along the ionizing bar, is not hand held, nor mobile, and cannot sense both the ion flow from an emitter point of the static eliminator device and the presence of an emitter voltage at an emitter point to accurately detect both the fouling of an emitter point and a shorted emitter point.

Figure 10:
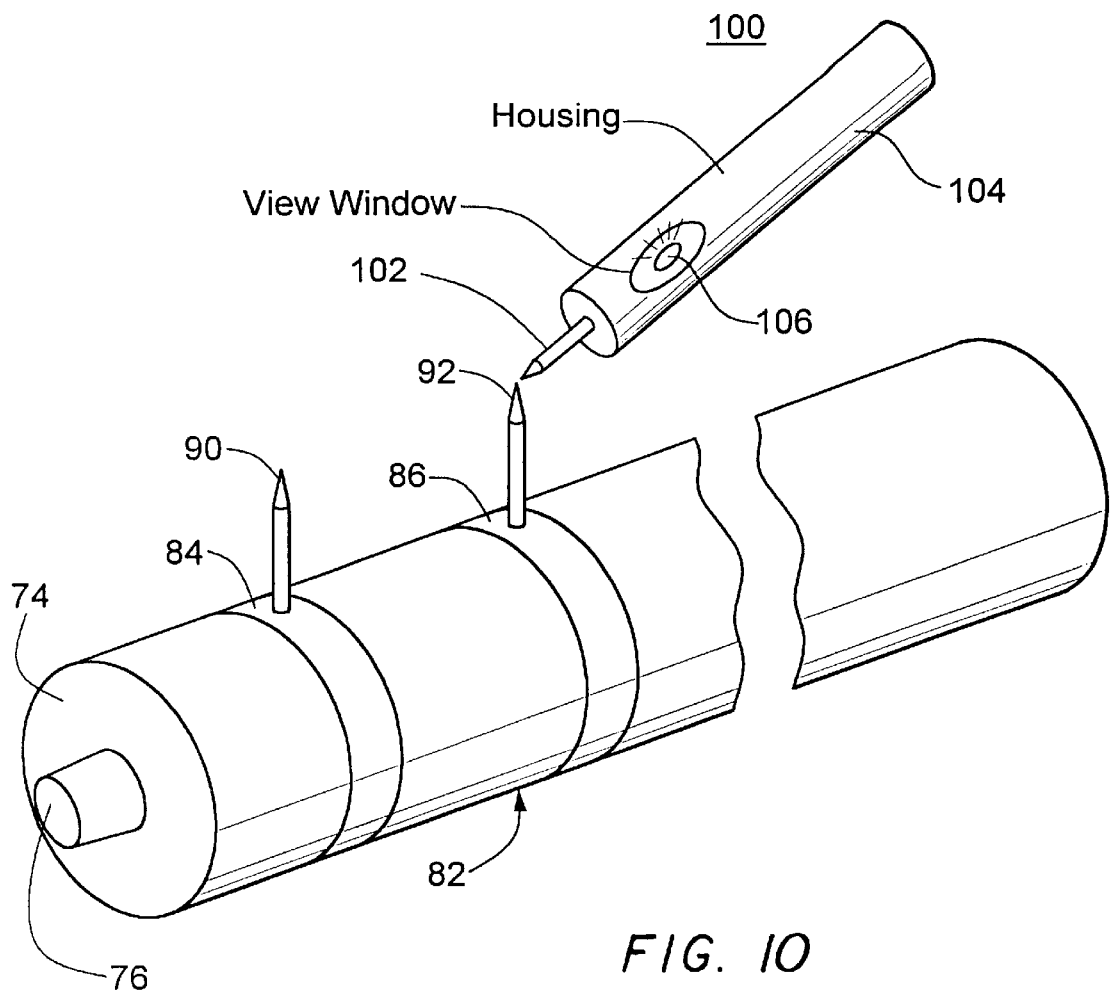
FIG. 10 is a schematic view of a prior art probe type indicator.
Figure 11:
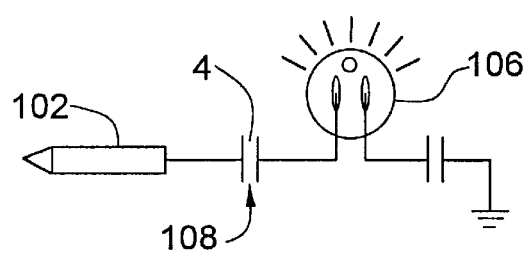
FIG. 11 is a wiring diagram of the prior art probe type indicator shown in FIG. 10.

Prior art indicator 100, FIG. 10 includes conductive probe 102 disposed at the end of a hand-held housing 104. Lamp 106, FIG. 10 and 11 is connected via spark gap 108 to conductive probe 102 at best provides only an indication of whether a voltage is present near the probe, and is not able to discern the presence or absence of an ion flow available from an ionizing point. Thus prior art indicator 100 is not capable of accurately detecting the fouling of a point.

In addition, the indicating neon bulb draws such a degree of current to provide illumination that significant capacitive coupling to AC is required, and the probe is not of a sufficient size to gather meaningful ion current with respect to the bulb illumination current. Thus, if emitter point 90 is fouled, the neon indicator of this prior art device may still glow, giving a false positive indicia. When the operator places the probe near a wire carrying high voltage AC, the capacitive coupling of the probe to the wire will also cause illumination of the neon bulb.

Figure 12:
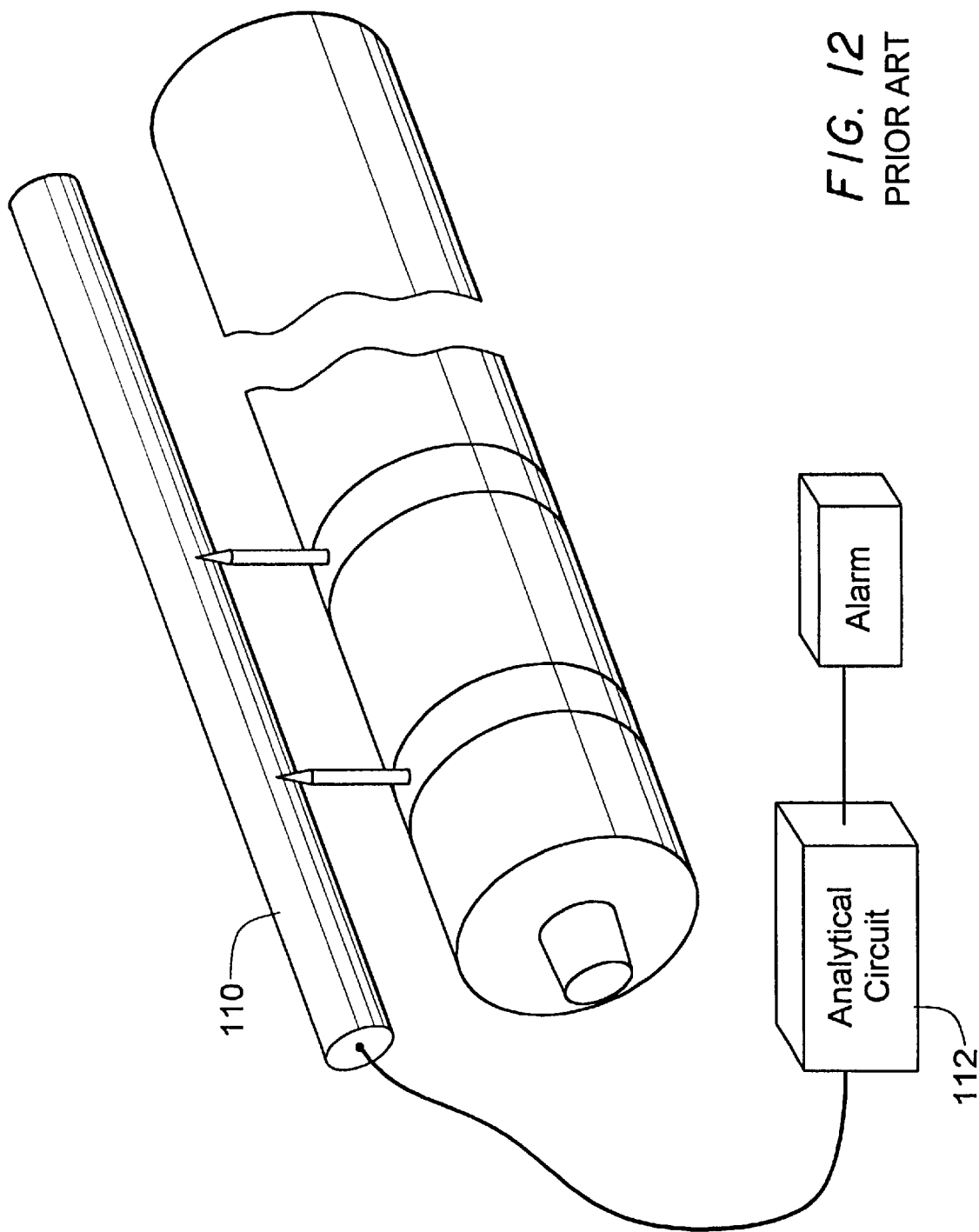
FIG. 12 is a schematic view of a prior art conductive rod type indicator.

Prior art conductive rod 110, FIG. 12 is positioned near the emitter points, and thus gathers both the capacitive coupling current from the nearby structure of the emitter points and bands, and also some portion of the ion current from the emitter points. The portion of ion current gathered must be held to a minimum, since only the remaining ungathered portion is useful for eliminating static electricity. Complex analytical circuit 112 then discerns which portion of the current is related to the ion current from the emitter point. Since conductive rod 110 extends the entire length of the static eliminating bar, the current from each emitter point and band is summed in such a way that there is no way to validate the ion output from any individual emitter point. The analytical circuitry is relatively large, and located remotely from the bar. See U.S. Pat. No. 5,017,876.

Although specific features of this invention are shown in some drawings and not others, this is for convenience only as each feature may be combined with any or all of the other features in accordance with the invention.

Other embodiments will occur to those skilled in the art and are within the following claims:

What is claimed is:

1. An electrical static eliminator device performance indicator comprising:
   a housing including:
      means for sensing the ion flow from an emitter point of the static eliminator device and also for sensing the presence of voltage at an emitter point to accurately detect the fouling of an emitter point or a shorted emitter point, and
      a display, responsive to the means for sensing, for displaying an indication of a fouled emitter point or a shorted emitter point; and means for sliding said housing along the static eliminator device and for positioning the means for sensing at a predetermined distance from the body of the static eliminator device to provide an indication of whether each emitter point of the static eliminator device is ionizing.

2. The indicator of claim 1 in which said means for sliding includes at least one clip attached on one end to the housing having another end configured to slidably engage the static eliminator device.

3. The indicator of claim 1 further including an extender for the means for sensing.

4. An electrical static eliminator device performance indicator comprising:
   means for sensing the ion flow from one or more emitter points of the static eliminator device and also for sensing the presence of a voltage at one or more emitter points to accurately detect either the fouling of an emitter point or a shorted emitter point;
   a display, responsive to the means for sensing, for displaying an indication of a fouled emitter point or a shorted emitter point; and
   an electrical circuit interconnecting the means for sensing and the display, the electrical circuit including a first resistor connected between the display and ground for removing residual charges from the display.

5. The indicator of claim 4 in which the electrical circuit includes a voltage divider.

6. The indicator of claim 5 in which the voltage divider includes a second resistor connected between the sensor and the display.

7. An electrical static eliminator device performance indicator comprising:
   means for sensing the ion flow from one or more emitter points of the static eliminator device and also for sensing the presence of a voltage at one or more emitter points to accurately detect either the fouling of an emitter point or a shorted emitter point;
   a display, responsive to the means for sensing, for displaying an indication of a fouled emitter point or a shorted emitter point;
   an electrical circuit interconnecting the means for sensing and the display; and
   a housing for integrating said means for sensing, said display, and said electrical circuit in a mobile fashion for sensing the performance of the static eliminator device along its length, the housing including a window on one surface thereof for viewing the display and a set of depending legs configured to engage a shield portion of the static eliminator device and to position the means for sensing a predetermined distance from the emitter points of the static eliminator device.

8. An electrical static eliminator device performance indicator comprising:
   means for sensing the ion flow from one or more emitter points of the static eliminator device and also for sensing the presence of a voltage at one or more emitter points to accurately detect either the fouling of an emitter point or a shorted emitter point;
   a display, responsive to the mean, for sensing, for displaying an indication of a fouled emitter point or a shorted emitter point;
   an electrical circuit interconnecting the means for sensing and the display; and
   a housing for integrating said means for sensing, said display, and said electrical circuit in a mobile fashion for sensing the performance of the static eliminator device along its length, said housing including a set of depending legs configured to engage a shield portion of the static eliminator device and to position the means for sensing a predetermined distance from the emitter points of the static eliminator device.

9. An electrical static eliminator device performance indicator comprising:
   means for sensing the ion flow from one or more emitter points of the static eliminator device and also for sensing the presence of a voltage at one or more emitter points to accurately detect either the fouling of an emitter point or a shorted emitter point, the means for sensing including a conductive plate and an extender for the conductive plate;
   a display, responsive to the means for sensing, for displaying an indication of a fouled emitter point or a shorted emitter point; and an electrical circuit interconnecting the means for sensing and the display.

10. An electrical static eliminator device performance indicator comprising:

means for sensing at least one of a) the ion flow from one or more emitter points of the static eliminator device and b) the electrical field from one or more emitter point bands of the static eliminator device;

a low current display, responsive to the means for sensing, for displaying an indication of a fouled emitter point or a shorted emitter point; and an electrical circuit interconnecting the means for sensing and the low current display for passively powering the display by deriving power from the electrical field energy created by the static eliminator device, said electrical circuit including a first resistor connected between the display and ground for removing residual charges from the display.

11. The indicator of claim 10 in which the electrical circuit includes a voltage divider.

12. The indicator of claim 11 in which the voltage divider includes a second resistor connected between the sensor and the display.

13. An electrical static eliminator device performance indicator comprising:

means for sensing at least one of a) the ion flow from one or more emitter points of the static eliminator device and b) the electrical field from one or more emitter point bands of the static eliminator device, the means for sensing including a conductive plate and an extender for the conductive plate;

a low current display, responsive to the means for sensing, for displaying an indication of a fouled emitter point or a shorted emitter point; and an electrical circuit interconnecting the means for sensing and the low current display for passively powering, the display by deriving power from the electrical field energy created by the static eliminator device.

14. An electrical static eliminator device performance indicator comprising:

means for sensing at least one of a) the ion flow from one or more emitter points of the static eliminator device and b) the electrical field from one or more emitter point bands of the static eliminator device;

a low current display, responsive to the means for sensing, for displaying an indication of a fouled emitter point or a shorted emitter point;

an electrical circuit interconnecting the means for sensing and the low current display for passively powering; the display by deriving power from the electrical field energy created by the static eliminator device; and a housing for integrating said means for sensing, said display, and said electrical circuit in a mobile fashion for sensing the performance of the static eliminator device along its length, the housing including a window on one surface thereof for viewing the display and a set of depending legs configured to engage a shield portion of the static eliminator device and to position the means for sensing a predetermined distance from the emitter points of the static eliminator device.

* * * * *